United States Patent
Norgeot et al.

(10) Patent No.: US 11,461,496 B2
(45) Date of Patent: Oct. 4, 2022

(54) DE-IDENTIFICATION OF ELECTRONIC RECORDS

(71) Applicant: The Regents of the University of California, Oakland, CA (US)

(72) Inventors: Beau Norgeot, Palo Alto, CA (US); Atul Butte, San Francisco, CA (US); Gundolf Schenk, San Francisco, CA (US); Eugenia Rutenberg, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 273 days.

(21) Appl. No.: 16/897,153

(22) Filed: Jun. 9, 2020

(65) Prior Publication Data

US 2020/0394333 A1 Dec. 17, 2020

Related U.S. Application Data

(60) Provisional application No. 62/861,963, filed on Jun. 14, 2019.

(51) Int. Cl.
*G06F 21/62* (2013.01)
*G06F 21/33* (2013.01)
(Continued)

(52) U.S. Cl.
CPC .......... *G06F 21/6254* (2013.01); *G06F 21/33* (2013.01); *G06F 40/284* (2020.01); *G16H 10/60* (2018.01)

(58) Field of Classification Search
CPC ....... G16H 10/60; G06F 21/33; G06F 40/284; G06F 21/6254
See application file for complete search history.

(56) References Cited

U.S. PATENT DOCUMENTS 9,342,571 B1 5/2016 Kurtic et al.
10,599,767 B1 * 3/2020 Mattera ................. G06F 40/268
(Continued)

FOREIGN PATENT DOCUMENTS

WO WO-2020/251956 A1 12/2020

OTHER PUBLICATIONS

Aberdeen, J. et al. (Dec. 2010, e-published Oct. 14, 2010. "The MITRE Identification Scrubber Toolkit: design, training, and assessment," *Int J Med Inform.* 79(12):849-859.
(Continued)

*Primary Examiner* — Mohammad A Siddiqi
(74) *Attorney, Agent, or Firm* — Mintz Levin Cohn Ferris Glovsky and Popeo, P.C.

(57) ABSTRACT

A system is provided for de-identifying electronic records. The system may be configured to tokenize an electronic record to produce a plurality of tokens including a first token. The system may determine whether the first token is part of one of a plurality of expressions known to include protected health information. In response to determining that the first token is not part of any one of the plurality of expressions, the system may determine, based on a blacklist of tokens known to include protected health information, whether the first token includes protected health information. In response to determining that the first token includes protected health information, the system may generate a de-identified electronic record by replacing the first token with a second token obfuscating the protected health information. Related methods and computer program products are also provided.

18 Claims, 4 Drawing Sheets

(51) Int. Cl.
G16H 10/60 (2018.01)
G06F 40/284 (2020.01)

(56) References Cited

U.S. PATENT DOCUMENTS

| | | | | |
|---|---|---|---|---|
| 11,030,207 | B1* | 6/2021 | Setlur | G06F 16/248 |
| 11,120,144 | B1* | 9/2021 | Kassam-Adams | |
| | | | | G06F 21/6245 |
| 2012/0278102 | A1* | 11/2012 | Johnson | G16H 10/60 |
| | | | | 705/3 |
| 2015/0112870 | A1* | 4/2015 | Nagasundaram | G06Q 20/3821 |
| | | | | 705/67 |
| 2015/0324606 | A1 | 11/2015 | Grondin et al. | |
| 2016/0378853 | A1* | 12/2016 | Mohammad | G06F 16/3344 |
| | | | | 707/706 |
| 2017/0063840 | A1* | 3/2017 | Krishnaiah | G06Q 20/3674 |
| 2017/0091170 | A1* | 3/2017 | Cardillo | G06F 40/56 |

OTHER PUBLICATIONS

Afzal, N. et al. (Jul. 26, 2017). "Surveillance of Peripheral Arterial Disease Cases Using Natural Language Processing of Clinical Notes," *AMIA Jt Summits Transl Sci Proc.* 2017:28-36.

Deleger, L. et al. (Jan. 1, 2013, e-published Aug. 2, 2012). "Large-scale evaluation of automated clinical note de-identification and its impact on information extraction," *J Am Med Inform Assoc.* 20(1):84-94.

Deleger, L. et al. (Aug. 2014, e-published Feb. 17, 2014). "Preparing an annotated gold standard corpus to share with extramural investigators for de-identification research," *J Biomed Inform.* 50:173-183.

Dernoncourt, F. et al. (May 1, 2017). "De-identification of patient notes with recurrent neural networks," *J Am Med Inform Assoc.* 24(3):596-606.

Ferández O, et al. (Jul. 27, 2012). "Evaluating current automatic de-identification methods with Veteran's health administration clinical documents," *BMC Med Res Methodol.* 12:109.

Ferrucci, D. et al. (Sep. 2004). "UIMA: an architectural approach to unstructured information processing in the corporate research environment," *Natural Language Engineering* 10(3-4):327-348.

Finlayson, S.G et al. (Sep. 16, 2014). "Building the graph of medicine from millions of clinical narratives," *Sci Data.* 1:140032.

Goldberger, A.L et al. (Jun. 13, 2000). "PhysioBank, PhysioToolkit, and PhysioNet: components of a new research resource for complex physiologic signals," *Circulation* 101(23):E215-20.

"Guidance Regarding Methods for De-ldentification of Protected Health Information in Accordance with the Health Insurance Portability and Accountability Act (HIPAA) Privacy Rule," Guidance on De-Identification of Protected Health Information (Nov. 26, 2012), located at < http://www.webcitation.org/74K7D9KyU> 32 pages.

Iqbal, E. et al. (Nov. 9, 2017). "ADEPt, a semantically-enriched pipeline for extracting adverse drug events from free-text electronic health records," *PLoS One* 12(11):e0187121.

International Search Report dated Aug. 25, 2020, for PCT Application No. PCT/US2020/036849, filed Jun. 9, 2020, 3 pages.

Jung, K. et al. (Feb. 19, 2014). "Automated detection of off-label drug use," *PLoS One* 9(2):e89324.

Liu,Z. et al. (Nov. 2017, e-published Jun. 1, 2017). "De-Identification of clinical notes via recurrent neural network and conditional random field" *J Biomed Inform.* 75S:S34-S42.

McMurry, A.J. et al. (Oct. 2, 2013). "Improved de-identification of physician notes through integrative modeling of both public and private medical text," *BMC Med Inform Decis Mak.* 2013 13:112.

Meystre, S.M et al. (Aug. 2, 2010). "Automatic de-identification of textual documents in the electronic health record: a review of recent research," *BMC Med Res Methodol* 10:70.

Neamatullah I. et al. (Jul. 24, 2008). "Automated de-identification of free-text medical records," *BMC Med Inform Decis Mak.*8.32.

Rim, K. "MAE2:Portable Annotation Tool for General Natural Language Use," presented at Proceedings of the LREC 2016 Workshop, ISA-12 12th Joint ACL-ISO Workshop on Interoperable Semantic Annotation, May 28, 2016, Portoroz, Slovenia, 16 pages.

Savova, G.K. et al. Se—Oct. 2010). "Mayo clinical Text Analysis and Knowledge Extraction System (cTAKES): architecture, component evaluation and applications," *J Am Med Inform Assoc.* Sep.-Oct. 2010;17(5):507-13.

Sibanda, T. et al. (2006). "Role of local context in automatic deidentification of ungrammatical, fragmented text," Proceedings of the Human Language Technology Conference of the NAACL, Main Conference, pp. 65-73.

Stubbs, A. et al. (Dec. 2015, e-published Jul. 28, 2015). "Automated systems for the de-identification of longitudinal clinical narratives: Overview of 2014 i2b2/UTHealth shared task Track 1," *J Biomed Inform.* 58 Suppl:S11-9.

Stubbs, A. et al. (Dec. 2015, e-published Aug. 28, 2015). "Annotating longitudinal clinical narratives for de-identification: The 2014 i2b2/UTHealth corpus," *J Biomed Inform.* 58 Suppl:S20-S29.

Uzuner, O. et al. (Sep.-Oct. 2007, e-published Jun. 28, 2007). "Evaluating the state-of-the-art in automatic de-identification," *J Am Med Inform Assoc.* 14(5):550-563.

Written Opinion dated Aug. 25, 2020, for PCT Application No. PCT/US2020/036849, filed Jun. 9, 2020, 6 pages.

* cited by examiner

DE-IDENTIFICATION OF ELECTRONIC RECORDS

This application claims priority to and the benefit of U.S. Provisional Patent Application No. 62/861,963 which is entitled "DE-IDENTIFICATION OF ELECTRONIC RECORDS," and filed on Jun. 14, 2019, the disclosure of which is incorporated herein by reference for all purposes.

STATEMENT OF GOVERNMENT SPONSORED SUPPORT

This invention was made with government support under Award Number UL1 TR001872 awarded by the National Center for Advancing Translational Sciences of the National Institutes of Health. The government has certain rights in the invention.

TECHNICAL FIELD

The subject matter described herein relates generally to the de-identification of electronic records, including the de-identification of protected health information in electronic records.

BACKGROUND

Electronic records may include data useful to researchers and publishers, but may also include personal information and/or other sensitive information. According to some government and/or industry regulations, such personal or sensitive information must be removed or obfuscated from the electronic records prior to use in research, publication, and/or dissemination. For example, the Health Insurance Portability and Accountability Act of 1996 (HIPAA) requires the removal and/or obfuscation of protected health information (PHI) found in electronic records including, for example, names, addresses, any elements of dates related to an individual, telephone numbers, fax numbers, email addresses, Social Security Numbers, medical record numbers, health plan beneficiary numbers, account numbers, certificate or license numbers, vehicle or other device serial numbers, Web Uniform Resource Locators (URLs), Internet Protocol (IP) addresses, finger or voice prints, photographic images, and/or the like.

SUMMARY

Systems, methods, and articles of manufacture, including computer program products, are provided for de-identifying electronic records. In some example embodiments, there is provided a system that includes at least one processor and at least one memory. The at least one memory may include program code that provides operations when executed by the at least one processor. The operations may include: tokenizing an electronic record to produce a plurality of tokens including a first token; determining, whether a protected health information is included in the electronic record by at least determining whether the first token is part of one of a first plurality of expressions, each of the first plurality of expressions known to include the protected health information, and in response to determining that the first token is not part of any one of the first plurality of expressions, determining, based on a blacklist of tokens known to comprise the protected health information, whether the first token comprises the protected health information; and in response to determining that the first token comprises the protected health information, generating a de-identified electronic record by at least replacing the first token with a second token obfuscating the protected health information.

In some variations, one or more features disclosed herein including the following features can optionally be included in any feasible combination. In response to an incorrect identification of the protected health information, the first plurality of expressions may be updated by at least adding, to the first plurality of expressions, an expression including the first token and a third token adjacent to the first token in the electronic record.

In some variations, in response to an incorrect identification of the protected health information, the blacklist of tokens may be updated by at least adding the first token to the black list of tokens or removing the first token from the blacklist of tokens.

In some variations, in response to an incorrect identification of the protected health information, the blacklist may be applied before applying the first plurality of expressions.

In some variations, determining whether the first token includes the protected health information may further include assigning a part-of-speech to the first token. In response to an incorrect identification of the protected health information, the part-of-speech assigned to the first token may be modified by at least modifying a first part-of-speech tagging algorithm applied to assign the part-of-speech to the first token and/or changing the first part-of-speech tagging algorithm to a second part-of-speech tagging algorithm.

In some variations, whether the first token comprises the protected health information may be determined based on the blacklist of tokens known to include the protected health information in response to the first token being assigned a first part-of-speech. In response to an incorrect identification of the protected health information, the blacklist of tokens may be applied in response to the first token being assigned a second part-of-speech instead of the first part-of-speech.

In some variations, the de-identified electronic record may be generated to include the first token in response to determining that the first token includes a non-protected health information.

In some variations, in response to determining that the first token includes neither the protected health information nor a non-protected health information, the de-identified electronic record may be generated by at least replacing the first token with the second token obfuscating the protected health information.

In some variations, whether the first token includes a non-protected health information may be determined based on a whitelist of tokens known to include a non-protected health information.

In some variations, the first token may be determined to include the protected health information based at least on the first token being part of the one of the first plurality of expressions.

In some variations, whether the first token includes a non-protected health information may be determined by at least determining whether the first token is part of one of a second plurality of expressions. Each of the second plurality of expressions may be known to exclude the protected health information.

In some variations, whether the first token includes the protected health information may be further determined based on a notes map, wherein the notes map includes one or more note-specific unsafe regular expressions, one or more note-specific blacklists, and/or one or more note-specific parts of speech.

In another aspect, there is provided a method for de-identifying electronic records. The method may include: tokenizing an electronic record to produce a plurality of tokens including a first token; determining, whether a protected health information is included in the electronic record by at least: determining whether the first token is part of one of a first plurality of expressions, each of the first plurality of expressions known to include the protected health information, and in response to determining that the first token is not part of any one of the first plurality of expressions, determining, based on a blacklist of tokens known to comprise the protected health information, whether the first token comprises the protected health information; and in response to determining that the first token comprises the protected health information, generating a de-identified electronic record by at least replacing the first token with a second token obfuscating the protected health information.

In some variations, one or more features disclosed herein including the following features can optionally be included in any feasible combination. The method may further include responding to an incorrect identification of the protected health information by at least updating the first plurality of expressions. The first plurality of expressions may be updated by at least adding, to the first plurality of expressions, an expression including the first token and a third token adjacent to the first token in the electronic record.

In some variations, the method may further include responding to an incorrect identification of the protected health information by at least updating the blacklist of tokens. The blacklist of tokens may be updated by at least adding the first token to the blacklist of tokens or removing the first token from the blacklist of tokens.

In some variations, the method may further include responding to an incorrect identification of the protected health information by at least applying the blacklist of tokens before applying the first plurality of expressions.

In some variations, the method may further include determining whether the first token includes the protected health information by assigning a part-of-speech to the first token.

In some variations, the method may further include responding to an incorrect identification of the protected health information by at least modifying the part-of-speech assigned to the first token. The part-of-speech assigned to the first token may be modified by at least modifying a first part-of-speech tagging algorithm applied to assign the part-of-speech to the first token and/or changing the first part-of-speech tagging algorithm to a second part-of-speech tagging algorithm.

In some variations, the method may further include, in response to the first token being assigned a first part-of-speech, determining, based on the blacklist of tokens known to include the protected health information, whether the first token includes the protected health information.

In some variations, the method may further include responding to an incorrect identification of the protected health information by at least applying the blacklist of tokens in response to the first token being assigned a second part-of-speech instead of the first part-of-speech.

In some variations, the method may further include, in response to determining that the first token includes a non-protected health information, generating the de-identified electronic record to include the first token.

In some variations, the method may further include, in response to determining that the first token includes neither the protected health information nor a non-protected health information, generating the de-identified electronic record by at least replacing the first token with the second token obfuscating the protected health information.

In some variations, the method may further include determining, based on a whitelist of tokens known to include a non-protected health information, whether the first token includes a non-protected health information.

In some variations, the method may include determining the first token includes the protected health information based at least on the first token being part of the one of the first plurality of expressions.

In some variations, the method may further include determining whether the first token includes a non-protected health information by at least determining whether the first token is part of one of a second plurality of expressions. Each of the second plurality of expressions may be known to exclude the protected health information.

In some variations, the method may further include determining whether the first token includes protected health information based on a notes map. The notes map may include one or more note-specific unsafe regular expressions, one or more note-specific blacklists, and/or one or more note-specific parts of speech.

In another aspect, there is provided a non-transitory computer readable storage medium. The non-transitory computer-readable storage medium may include instructions that causes operations when executed by at least one data processor. The operations may include: tokenizing an electronic record to produce a plurality of tokens including a first token; determining, whether a protected health information is included in the electronic record by at least: determining whether the first token is part of one of a first plurality of expressions, each of the first plurality of expressions known to include the protected health information, and in response to determining that the first token is not part of any one of the first plurality of expressions, determining, based on a blacklist of tokens known to comprise the protected health information, whether the first token comprises the protected health information; and in response to determining that the first token comprises the protected health information, generating a de-identified electronic record by at least replacing the first token with a second token obfuscating the protected health information.

In another aspect, there is provided an apparatus. The apparatus may include: means for tokenizing an electronic record to produce a plurality of tokens including a first token; means for determining, whether a protected health information is included in the electronic record by at least determining whether the first token is part of one of a first plurality of expressions, each of the first plurality of expressions known to include the protected health information, and in response to determining that the first token is not part of any one of the first plurality of expressions, determining, based on a blacklist of tokens known to comprise the protected health information, whether the first token comprises the protected health information; and means for, in response to determining that the first token comprises the protected health information, generating a de-identified electronic record by at least replacing the first token with a second token obfuscating the protected health information.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Electronic records may include information needed for research and/or publication. For example, an electronic record may include one or more strings of tokens that correspond to patient test results, observations, medical narratives, descriptions of patient experience, and/or event timelines. Government and/or industry regulations may require the removal and/or obfuscation of at least some tokens included in an electronic record before information included in the electronic record may be used for research, publication, and/or dissemination. As such, electronic records may undergo de-identification prior to being made available for research, publication, and/or dissemination. However, conventional de-identification techniques may be unable to successfully identify tokens corresponding to protected health information (PHI), which require removal and/or obfuscation. For instance, the identification of tokens corresponding to protected health information may be complicated by the large number of tokens and token combinations that may be considered protected health information, variations between different types of electronic records, variations between different patient populations, variations between different health systems, and variations between departments within a given health system.

In some example embodiments, a processing engine may be configured to identify, in an electronic record, one or more tokens corresponding to protected health information. For example, the processing engine may identify a token as corresponding to protected health information based on one or more filters which include unsafe regular expressions. An unsafe regular expression may be used to identify tokens known to correspond to protected health information. Alternatively and/or additionally, the processing engine may identify a token as corresponding to non-protected health information based on one or more filters which include safe regular expressions. A safe regular expression may be used to identify tokens known to correspond to non-protected health information.

Furthermore, the processing engine may identify a token as corresponding to protected health information based on one or more blacklists of known protected health information tokens. The processing engine may also identify a token as corresponding to non-protected health information based on one or more whitelists of known non-protected health information tokens. Prior to rendering the electronic record available for research, publication, and/or dissemination, the processing engine may remove and/or obfuscate the tokens that correspond to protected health information while preserving the tokens that correspond to non-protected health information.

Figure 1:
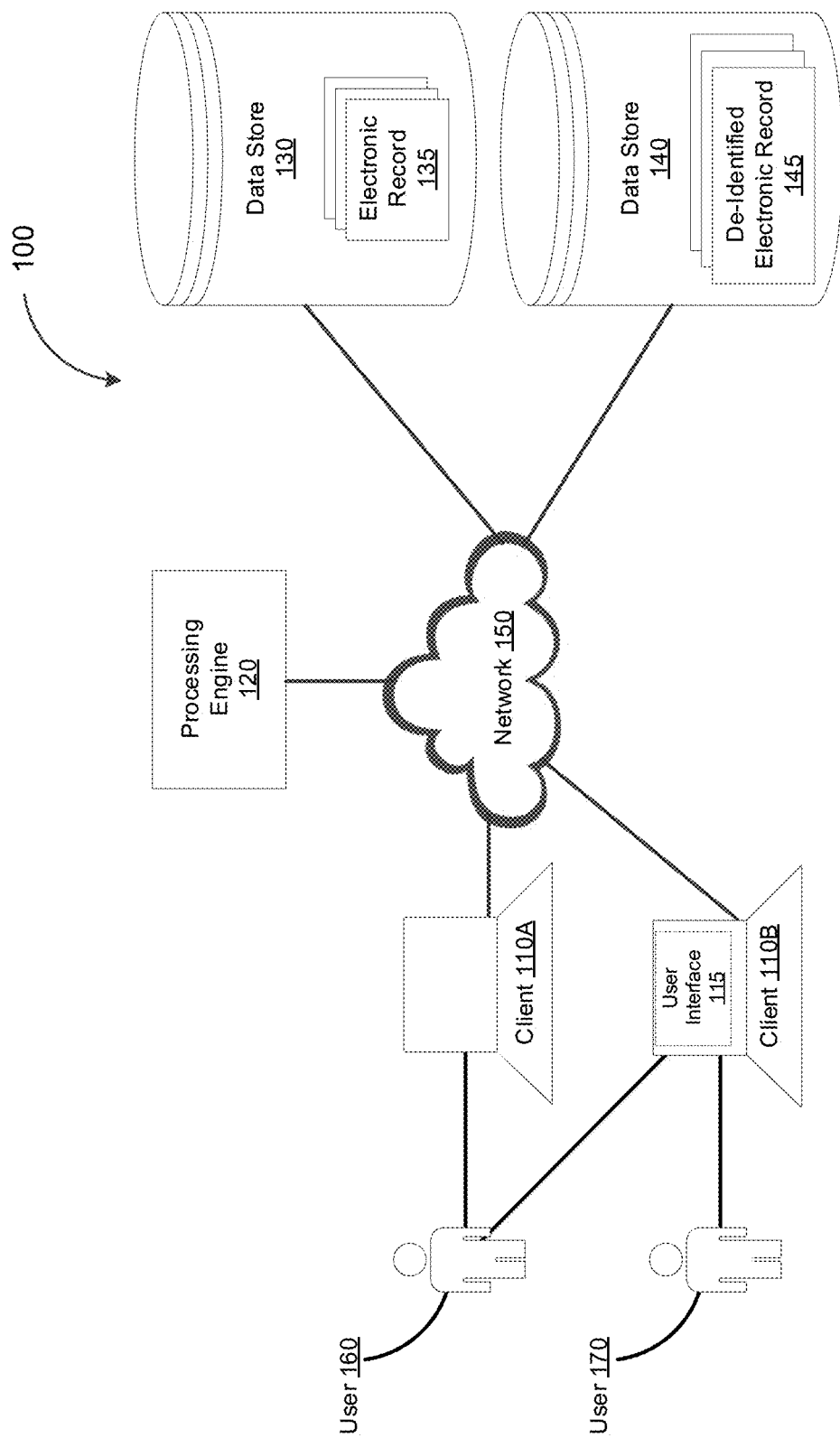
FIG. 1 depicts a system diagram illustrating an example of a de-identification system, in accordance with some example embodiments.

FIG. 1 depicts a system diagram illustrating an example of a de-identification system 100, in accordance with some example embodiments. Referring to FIG. 1, the de-identification system 100 may include clients 110A-B. Each of the clients 110A-B may be a processor-based device including, for example, a computer, a smartphone, a tablet computer, a wearable, a virtual assistant, an Internet-of-Things (IoT) appliance, and/or the like. The clients 110A-B may be communicatively coupled to a processing engine 120 via a network 150. The network 150 may include a wired and/or wireless network including, for example, a local area network (LAN), a virtual local area network (VLAN), a wide area network (WAN), a public land mobile network (PLMN), the Internet, and/or the like. Although FIG. 1 may depict a remote and/or cloud-based deployment of the processing engine 120 in which the processing engine 120 is accessed via the network 150, it should be appreciated that at least a portion of the functionalities associated with the processing engine 120 may be deployed locally, for example, at the clients 110A-B as software, hardware, or a combination thereof.

Referring again to FIG. 1, a first user 160 at the first client 110A may provide, to the first client 110A, an input identifying an electronic record 135 stored in a first data store 130. The electronic record 135 may be an electronic health record including protected health information and/or non-protected health information. The first client 110A may send a start indication to the processing engine 120. In response to receiving the start indication from the first client 110A, the processing engine 120 may access the first data store 130 to retrieve the electronic record 135. Furthermore, the processing engine 120 may de-identify the electronic record 135 and generate a de-identified electronic record 145, which may include identifying, removing, and/or obfuscating one or more tokens included in the electronic record 135 that correspond to protected health information. The processing engine 120 may store the de-identified electronic record 145 in a second data store 140. Alternatively and/or additionally, the processing engine 120 may generate and/or update a user interface 115, which may be displayed at the second client 110B to at least enable the first user 160 and/or a second user 170 to view the de-identified record 145.

In some example embodiments, in order to improve security and/or in order to restrict access to the electronic record 135, prior to de-identification, the clients 110A-B, the processing engine 120, the first data store 130, the second data store 140, and/or the network 150 may be isolated from other computers and/or other networks, including, for example, isolated from the Internet.

Figure 2:
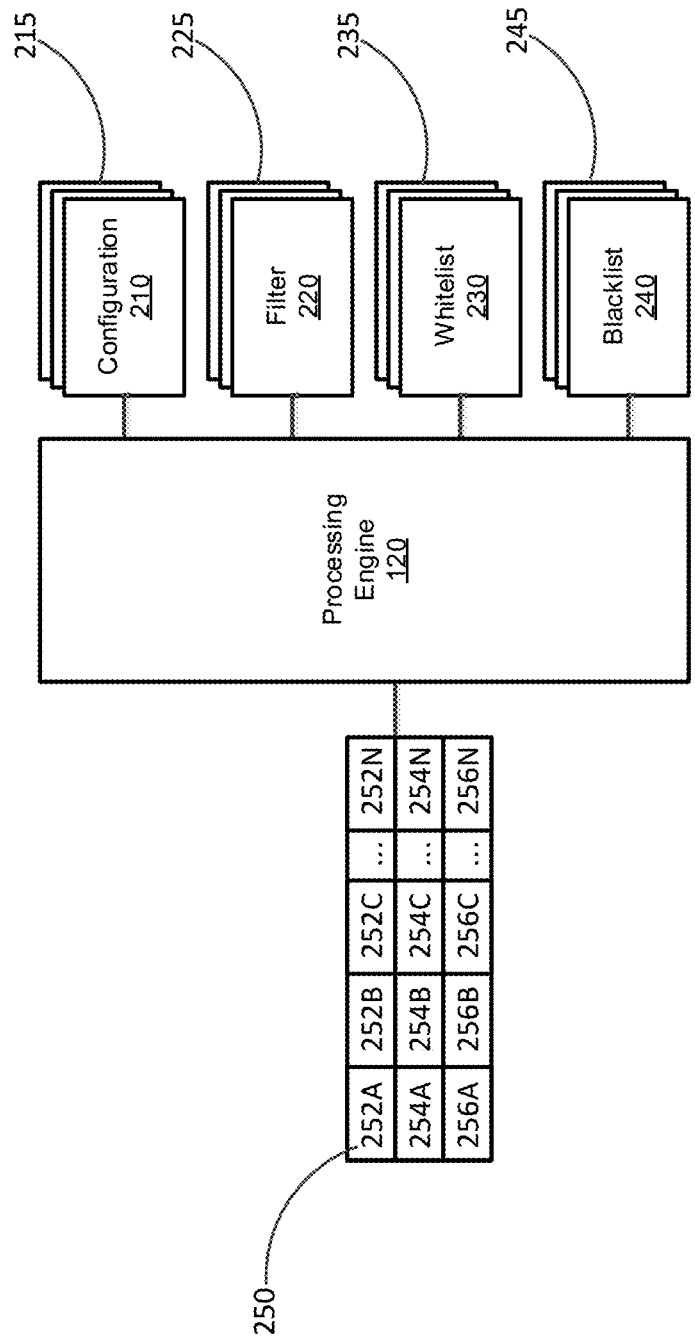
FIG. 2 depicts a block diagram illustrating an example of a processing engine, in accordance with some example embodiments.

To further illustrate, FIG. 2 depicts a block diagram illustrating an example of the processing engine 120. In some example embodiments, the processing engine 120 may load configuration information from a de-identification configuration 210. The de-identification configuration 210 may be used to configure a de-identification process, including by specifying a sequence of operations performed during the de-identification process. The de-identification configuration 210 may be included in a de-identification configuration library 215. The de-identification configuration 210 may include, for example, one or more text files, JavaScript Object Notation (JSON) files, Extensible Markup Language (XML) files, and/or the like.

In some example embodiments, the de-identification configuration 210 may be used to configure the processing engine 120 to de-identify the electronic records based on specific types of electronic records and/or based on specific uses of the de-identified electronic records. For example, the processing engine 120 may be configured to de-identify electronic records based on the type of institution (for example, a clinic and/or a hospital), the type of information included in the electronic record 135 (for example, electronic health records, clinical notes and/or patient records), applicable laws and/or regulations (for example, HIPAA), types of departments (for example, surgery and/or radiology), a specific department within an institution, the type of research being conducted using the de-identified electronic record 145, patient demographics, and/or the like. As such, different de-identification configurations may be used to remove more or less protected health information from the electronic record 135 depending on the source of the electronic record 135 and/or the intended use of the de-identified electronic record 145. Furthermore, various de-identification configurations may be used during optimization of the de-identification process and/or the processing engine 120.

In some example embodiments, the de-identification configuration 210 may be used to configure the processing engine 120 to de-identify the electronic record 135 based on the identity of a person as indicated, for example, by the person's name, social security number, patient identifier, and/or the like.

In some example embodiments, the processing engine 120 may tokenize the electronic record 135 to identify one or more tokens included in the electronic record 135. Each token may correspond to a word and/or a number, which may be separated from adjacent words and/or numbers by a delimiting character (e.g., a whitespace and/or the like) or a special character (e.g., symbols, punctuation marks, and/or the like). Accordingly, as used herein, "tokenize" or "tokenizing" may refer to separating each string included in the electronic record 135 into individual words and/or numbers.

Furthermore, the processing engine 120 may scan the tokens included in the electronic record 135. As each token is scanned, the processing engine 120 may initialize a token in a token array 250 with a reference to the corresponding word and/or number in the electronic record 135.

Each element of the token array 250 may have a corresponding token status 254A-N. As the processing engine 120 initializes each token in the token array 250, the processing engine 120 may initialize the token status 254A-N to an initial value, for example UNKNOWN, indicating no decision has been made with respect to whether the token corresponds to protected health information. For example, if the electronic record 135 includes the string "Mr. John Wayne", the processing engine 120 may store "Mr", "John", and "Wayne" as separate tokens in the token array 250 and set the corresponding token status 254A-N to UNKNOWN.

In some example embodiments, the processing engine 120 may analyze the structure of sentences found in the electronic record 135, identify a part of speech of a token in the token array 250, and set a corresponding parts of speech tag 256A-N accordingly. For example, the processing engine 120 may apply one or more part-of-speech tagging algorithms to identify a token as a noun, verb, adjective, proper noun, and/or the like. For example, the processing engine 120 may identify a token as an adjective if the token corresponds to the word "White" in the context of "White fluid found at . . . ." On the other hand, the processing engine 120 may identify a token as a proper noun if the token corresponds to the word "White" in the context of "Patient John White." The processing engine 120 may use the parts of speech tag 256A-N to narrow the meaning of a token based on the context of the token in the electronic record 135. For example, if a token corresponding to the word "White" is tagged as a proper noun, the processing engine 120 may determine that the token corresponds to protected health information. On the other hand, if the token is tagged as an adjective, the processing engine 120 may determine that the word "White" does not correspond to protected health information.

In some example embodiments, the one or more part-of-speech tagging algorithms may include one or more statistical natural language processing algorithms (e.g., included in the Python Natural Language Toolkit and/or the like) configured to assign a parts of speech tag to each token in the token array 250. Alternatively and/or additionally, the one or more part-of-speech tagging algorithms may include a machine learning model trained to assign the parts of speech tag to each token in the token array 250. Examples of the machine learning model include a recurrent neural network, a Bayesian network, a maximum entropy Markov model, a conditional random field, and a support vector machine.

In some example embodiments, the processing engine 120 may apply a filter 220 from a filters library 225 to identify each token in the token array 250 which corresponds to protected health information and/or non-protected health information. The filter 220 may include one or more safe regular expressions and/or unsafe regular expressions. As used herein, a safe regular expression may correspond to a regular expression that may be used to identify tokens corresponding to non-protected health information. On the other hand, an unsafe regular expression may correspond to a regular expression that may be used to identify tokens corresponding to protected health information.

In some example embodiments, the filter 220 may include a unsafe regular expression. As such, the processing engine 120 may apply the filter 220 to identify one or more tokens in the token array 250 that correspond to protected health information based on the token and/or the context of the token. The context of the token may include, for example, adjacent tokens and/or other nearby tokens. As noted, if, based on the filter 220, the processing engine 120 determines a token corresponds to protected health information, the processing engine 120 may set the corresponding token status 254A-N to a value, for example, PHI, indicating the token may need to be obfuscated when generating the de-identified electronic record 145. For example, tokens 252A-B may correspond to the words "age 97". As such, the token 252A may correspond to the word "age" and the token 252B may correspond to the number "97". Based a the safe filter, the processing engine 120 may determine that the token 252B corresponds to an age and, since patient age greater than 89 may be considered protected health information, the token 252B may correspond to protected health information. As such, the processing engine 120 may set the corresponding token status 254B to PHI, indicating the token 252B (e.g., "97") may need to be obfuscated when generating the de-identified electronic record 145.

In some example embodiments, the filter 220 may include a safe regular expression. As such, the processing engine 120 may apply the filter 220 to detect one or more tokens in the token array 250 that correspond to non-protected health information. If, based on the filter 220, the processing engine 120 determines that a token corresponds to non-protected health information, the processing engine 120 may set the corresponding token status 254A-N to a value, for example, SAFE, indicating the token may not need to be obfuscated when generating the de-identified electronic record 145. For example, the electronic record 135 may include the phrase "50 mg" and the tokens 252A-B may correspond to the strings "50" and "mg", respectively. The processing engine 120 may determines that the tokens 252A-B may be considered a dosage, and therefore may not be considered protected health information. As such, the processing engine 120 may set the corresponding token status 254A-B to SAFE, indicating the tokens 252A-B may not need to be obfuscated when generating the de-identified electronic record 145.

In some example embodiments, the processing engine 120 may determine whether a token appears in a whitelist 230, which may include one of a plurality of whitelists in a whitelist library 235. The whitelist 230 may include one or more tokens that are known to correspond to non-protected health information. Accordingly, if the processing engine 120 determines that the token does appear in the whitelist 230, the processing engine 120 may identify the token as corresponding to non-protected health information and, as such, may not need to be obfuscated when generating the de-identified electronic record 145. For example, the whitelist 230 may include a list of tokens corresponding to common English words which are known to not provide clues as to the identify a particular person. If the processing engine 120 determines that the whitelist 230 includes one of the tokens in the token array 250, the processing engine 120 may set the corresponding token status 254A-N to a value, for example, SAFE, indicating the token may not need to be obfuscated when generating the de-identified electronic record 145. It should be appreciated that the whitelist 230 may also include other types of tokens including, for example, common medical terms, common medical abbreviations, common English verbs with conjugations, and/or the like.

In some example embodiments, the processing engine 120 may determine whether a token appears in a blacklist 240, which may be one of a plurality of blacklists in a blacklist library 245. The blacklist 240 may include one or more tokens that are known to correspond to protected health information. Accordingly, if the processing engine 120 determines that the token appears in the blacklist 240, the processing engine 120 may determine that the token corresponds to protected health information that may need to be obfuscated when generating the de-identified electronic record 145. For example, the blacklist 240 may include one or more tokens corresponding to known first names. If the processing engine 120 determines that the blacklist 240 includes one of the tokens in the token array 250, the processing engine may set the corresponding token status 254A-N to a value, for example, BLACKLIST, indicating the token corresponds to protected health information that may need to be obfuscated when generating the de-identified electronic record 145. It should be appreciated that the blacklist 240 may also include other types of tokens considered protected health information, including, for example, known last names, location names, institution names, building or facility names, street addresses, street names, city names, country names, and/or the like.

Figure 3:
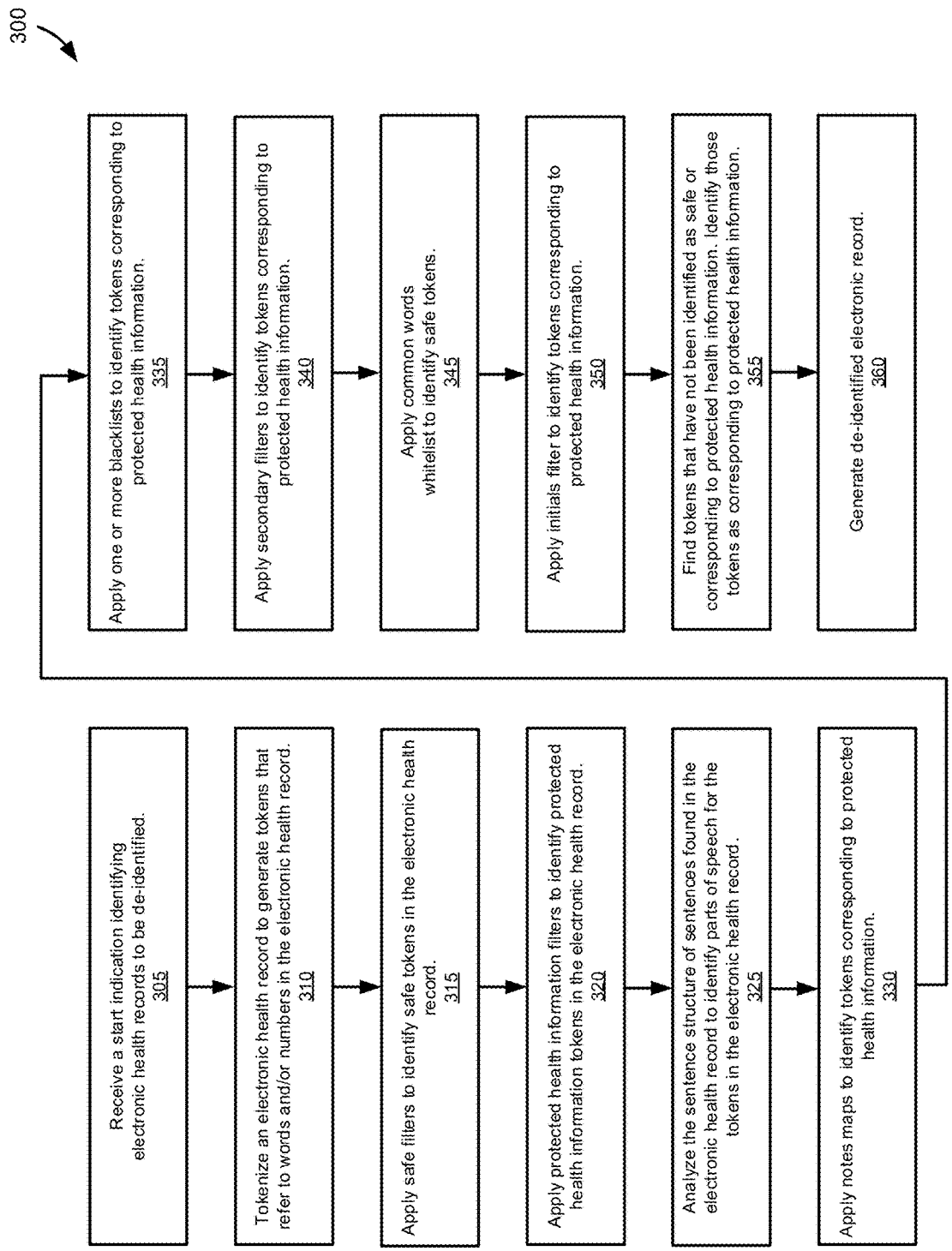
FIG. 3 depicts a flowchart illustrating an example of a process for de-identifying n electronic record, in accordance with some example embodiments.

FIG. 3 depicts a flowchart illustrating an example of a process for de-identifying the electronic record 135, in accordance with some example embodiments. The electronic record 135 may be an electronic health record including protected health information and/or non-protected health information.

At 305, the processing engine 120 may receive, from the first client 110A, a start indication may identify one or more electronic records to be de-identified. In some examples embodiments, the start indication may further identify the de-identification configuration 210, which may, as noted, specify a sequence and/or order of operations performed during the de-identification process.

In some example embodiments, the de-identification configuration 210 may be used to configure the processing engine 120 to de-identify electronic records based on the type of the electronic records and/or based on the specific uses of the de-identified electronic records. For example, the processing engine 120 may be configured to de-identify electronic records based on the type of institution, the type of information included in the electronic record 135, applicable laws and/or regulations, types of departments, a specific department within an institution, the type of research being conducted using the de-identified electronic record 145, patient demographics, and/or the like. As such, different de-identification configurations may be used to remove more or less protected health information from the electronic record 135 depending on, for example, the source of the electronic record 135 and/or the intended use of the de-identified electronic record 145. Furthermore, various de-identification configurations may be used during optimization of the de-identification system 100.

At 310, the processing engine 120 may tokenize the electronic record 135 to generate tokens that correspond to words and/or numbers in the electronic record 135. Each token may correspond to a word and/or a number, which may be separated from adjacent words and/or numbers by a delimiting character (e.g. whitespace, and/or the like) and/or a special character (e.g. symbols, punctuation marks, and/or the like.) Furthermore, the processing engine 120 may scan the tokens included in the electronic record 135. As each token is scanned, the processing engine 120 may initialize a token in the token array 250 with a reference to the corresponding word and/or number in the electronic record 135.

As the processing engine 120 initializes each token in the token array 250, the processing engine 120 may initialize the token status 254A-N for each token to an initial value, for example, UNKNOWN, indicating no decision has been made with respect to whether the token in the token array 250 corresponds to protected health information.

At 315, the processing engine 120 may apply one or more safe filters to identify safe tokens in the electronic record 135. As used herein, a safe filter may include a filter, for example, the filter 220, that includes a safe regular expression. As used herein, a safe token may include a token that does not correspond to protected health information. As such, the processing engine 120 may apply the safe filter to identify one or more safe tokens in the token array 250 which correspond to words or phrases that may not correspond to protected health information and may not need to be obfuscated when generating the de-identified electronic record 145. As such, the tokens identified by the safe filter may correspond to non-protected health information. If, based on the safe filter, the processing engine 120 determines that a token corresponds to non-protected health information, the processing engine 120 may set the corresponding token status 254A-N to a value, for example, SAFE, indicating the token may not need to be obfuscated when generating the de-identified electronic record 145. For example, the electronic record 135 may include a pain scale (e.g. "pain 10/10"). If, based on the safe filter, the processing engine 120 determines that one of the tokens in the token array 250 corresponds to a pain scale and, as such, does not correspond to protected health information, the processing engine 120 may set the corresponding token status 254A-N to SAFE. In some example embodiments, the filters library 225 may include one or more safe filters.

At 320, the processing engine 120 may apply one or more protected health information filters to identify protected health information tokens in the electronic record 135. As used herein, a protected health information filter may be a filter, for example the filter 220, that includes an unsafe regular expression. As used herein, a protected health information token may include a token that corresponds to protected health information. As such, the processing engine 120 may apply the protected health information filter to identify one or more protected health information tokens that correspond to words and/or numbers in the electronic record 135 that may include protected health information. For example, one or more protected health information filters may identify tokens that correspond to an email address, a phone number, a date of birth, a social security number, a postal code and/or the like. If, based on the protected health information filter, the processing engine 120 determines that one of the tokens in the token array 250 corresponds to protected health information, the processing engine 120 may set the corresponding token status 254A-N to a value, for example, PHI, indicating the token may need to be obfuscated when generating the de-identified electronic record 145. In some example embodiments, the filters library 225 may include one or more protected health information filters.

At 325, the processing engine 120 may analyze the sentence structure of sentences found in the electronic record 135 to identify parts of speech for the tokens in the electronic record 135. Based on identifying the parts of speech, the processing engine 120 assign a parts of speech tag to the corresponding token in the token array 250. For example, the processing engine 120 may determine that a token in the token array 250 corresponds to a noun, verb, adjective, pronoun, proper noun, and/or the like and set the corresponding parts of speech tag 256A-N accordingly. As noted, in some example embodiments, the processing engine 120 may use the parts of speech tags 256A-N to narrow the meaning of one or more tokens, for example, based on the context of the tokens in a sentence and/or the electronic record 135. For example, the processing engine 120 may identify a token as an adjective if the token corresponds to the word "White" in the context of "White fluid found at . . . ." On the other hand, the processing engine 120 may identify a token as a proper noun if the token corresponds to the word "White" in the context of "Patient John White." As noted, in some example embodiments, the processing engine 120 may include a statistical natural language processing system and/or a machine learning model trained to assign the parts of speech tag 256A-N to each token in the token array 250.

At 330, the processing engine 120 may apply a notes map to identify tokens corresponding to protected health information. In some example embodiments, a notes map may include one or more filters. Each filter may include one or more note-specific unsafe regular expressions and/or note-specific safe regular expressions. Alternatively and/or additionally, the notes map may include one or more note-specific blacklists and/or one or more note-specific whitelists.

In some example embodiments, the notes map may include an indication to use the context of a token to determine whether the token corresponds to protected health information. For example, if the processing engine 120 determines that a token is included in a note-specific blacklist, and/or if the processing engine 120 determines that the token is included in a note-specific unsafe regular expression, the processing engine 120 may determine whether the token is near (e.g. adjacent to) another token that has already been identified as corresponding to protected health information. If so, the processing engine 120 may identify the token as corresponding to protected health information.

In some example embodiments, the notes map may include an indication to use note-specific parts of speech tags to determine whether the token includes protected health information. For example, if the processing engine 120 has tagged the token with a particular part of speech tag (e.g. a pronoun or an adjective), and the processing engine 120 determines that a token appears in a note-specific blacklist, and/or if the processing engine determines that the token is included in a note-specific unsafe regular expression, the processing engine 120 may identify the token as corresponding to protected health information.

At 335, the processing engine 120 may apply one or more blacklists to identify tokens that correspond to protected health information. For example, the processing engine 120 may search the token array 250 to identify tokens that have been tagged as belonging to a particular part of speech (e.g. a proper noun or a noun) during the parts of speech analysis. If a token has been tagged as belonging to a particular part of speech, the processing engine 120 may determine whether the token appears in the blacklist 240. The blacklist 240 may include, for example, tokens corresponding to known first names, known last names, street names, street addresses, locations, and/or the like. Alternatively and/or additionally, the blacklist 240 may include tokens corresponding to patient information. For example, the blacklist 240 may include the name, identification number, social security number, street address, street name, and/or location of patients obtained from a patient database. Alternatively and/or additionally, the blacklist 240 may include tokens corresponding to protected health information obtained from a staff database. Alternatively and/or additionally, the blacklist 240 may include tokens corresponding to protected health information from other data sources.

In some example embodiments, the parts of speech tag 256A-N may indicate the token corresponds to particular part of speech, for example, a noun or a proper noun. If the processing engine 120 determines that the token is included in the blacklist 240, the processing engine 120 may set the corresponding token status 254A-N to a value, for example, PHI or BLACKLIST, indicating the token may need to be obfuscated when generating the de-identified electronic record 145.

In some examples embodiments, the blacklist library 245 may include separate blacklists for known first names, known last names, patient names, staff names, street names, locations, street addresses, and/or the like. As should be appreciated, the patient blacklist and/or the staff blacklist may be specific to, for example, a particular institution, a particular department within an institution, and/or the like. Also as should be appreciated, the known first blacklist and/or the known last blacklist may be specific to, for example, a region, a country, patient demographics and/or the like. In some example embodiments, the blacklist library 245 may include a patient-specific blacklist. Each patient-specific blacklist may be associated with a patient name and/or patient identifier. Each patient-specific blacklist may include tokens corresponding to protected health information of the patient, including the name, identification, names of friends and/or family members, phone numbers, email addresses, street address, location, social security number, insurance company name, insurance member number, employer name, and/or the like.

At 340, the processing engine 120 may apply one or more secondary filters to identify tokens corresponding to protected health information. As used herein, a secondary filter may include a filter, for example, the filter 220, which includes an unsafe regular expression that may be used to identify variations on names, street addresses, street names, locations, and/or the like. For example, the processing engine 120 may apply one or more secondary filters to identify tokens corresponding to name patterns, address patterns, location patterns, and/or the like that are known to appear in electronic records. If, based on the secondary filter, the processing engine 120 identifies a token as corresponding to protected health information, the processing engine 120 may set the corresponding token status 256A-N to a value, for example, PHI, indicating the token may need to be obfuscated when the de-identified electronic record 145 is generated. For example, the processing engine 120 may apply a secondary filter to determine whether a first token is near (e.g., adjacent to) a second token that has been marked as protected health information because, for example, the second token appears in the blacklist 240. If the second token has been marked as protected health information, the processing engine 120 may determine that the first token also corresponds to protected health information, and the processing engine 120 may set the corresponding token status 254A-N accordingly. For example, the tokens 252A-B may refer to the words "Jane" and "Doe", respectively. The token status 254A (e.g. corresponding to "Jane") may be set to BLACKLIST because, for example, the blacklist 240 includes a token referring to the name "Jane". The processing engine 120 may determine, based on the secondary filter, that the token 252B (e.g. corresponding to "Doe") corresponds to a because it is near a blacklisted token and, as a result, set the corresponding token status 254B (e.g. corresponding to "Doe") to PHI.

At 345, the processing engine 120 may apply a common words whitelist to identify safe tokens. In some example embodiments, the processing engine 120 may search the token array 250 for an unclassified token which, for example, has the corresponding token status 254A-N set to a value indicating that no decision has been made with respect to whether the token needs to be obfuscated when generating the de-identified electronic record 145. If the processing engine 120 detects an unclassified token in the token array 250, the processing engine 120 may search for the corresponding token in one or more whitelists to determine whether the token corresponds to non-protected health information. For example, if the processing engine 120 determines that the token status 254A-N of the token is set to the initial value, for example, UNKNOWN, the processing engine 120 may search the common words whitelist, for example, the whitelist 230, to determine whether the common words whitelist includes the token. If the processing engine 120 determines that the common words whitelist includes the token, the processing engine 120 may set the corresponding token status 254A-N to a value, for example, SAFE or WHITELIST, indicating the token may not need to be obfuscated when generating the de-identified electronic record 145.

In some example embodiments, the common words whitelist may also include common medical terms and abbreviations, common verbs, verb conjugations, and/or the like. In order to avoid incorrectly identifying a token as being safe, certain words may be excluded from the common words whitelist. The common words whitelist may include, for example, common English words, but may exclude known names, known street names, locations, and/or the like. For example, the common words whitelist may exclude include names, street addresses, locations, street names, and/or the like found in a Social Security database and/or a Census database.

At 350, the processing engine 120 may apply one or more initials filters to identify tokens corresponding to protected health information. As used herein, an initials filter, for example, the filter 220, may include an unsafe regular expression that can be used to identify tokens corresponding to one-letter initials of names, street names, locations, and/or the like. In some example embodiments, the processing engine 120 may apply the initials filter to determine whether a first token in the token array 250 corresponds to a single letter. If the first token is near (e.g., adjacent to) a second, blacklisted token, the processing engine 120 may mark the first token as protected health information. For example, the electronic record 135 may include the name "Susan A. Wallace", and the tokens 252A-C may correspond to "Susan", "A", and "Wallace", respectively. The token status 254A (e.g., corresponding to "Susan") may be set to BLACKLIST. The processing engine 120 may determine that the token 252B corresponds to a single letter (e.g., the letter "A") and determine that the adjacent token 252A (e.g., "Susan") has been marked as a blacklisted token. As such, the processing engine 120 may determine that the token 252B (e.g., "A") corresponds to protected health information and, as such, set the token status 254B (e.g., corresponding to the letter "A") to PHI, indicating the token 252B (e.g., "A") may need to be obfuscated when generating the de-identified electronic record 145.

At 355, the processing engine 120 may find any tokens in the token array 250 that have not been identified either as being safe or corresponding to protected health information and identify those tokens as corresponding to protected health information. In some example embodiments, the de-identification system 100 may treat patient privacy as having a higher priority than, for example, making additional information available for research, publication, and/or dissemination. If the token status 254A-N is set to an initial value indicating no decision has been made regarding whether the token corresponds to protected health information, the processing engine 120 may mark the token as corresponding to protected health information. For example, if the token status 254B is set to UNKNOWN, the processing engine 120 may set the token status to PHI, indicating the token may need to obfuscated when generating the de-identified electronic record 145.

At 360, the processing engine 120 may generate the de-identified electronic record 145 based on the token status 254A-N of each token in the token array 250. In some example embodiments, if a token is marked as corresponding to protected health information, the processing engine 120 may output an obfuscated token of the same length to the de-identified electronic record 145. Otherwise, if the token is marked as safe, the processing engine 120 may copy the token, for example, without obfuscating the token, from the electronic record 135 to the de-identified electronic record 145.

For example, the token 252A may correspond to the name "Susan", and the corresponding token status 254A may be set to PHI or BLACKLIST. When generating the de-identified electronic record 145, the processing engine 120 may output an obfuscation token of the same length as the token 252A (e.g., "*****").

In some example embodiments, the de-identification system 100 may optimize the de-identification process by applying machine learning techniques. Prior to optimization, a trained expert may produce a set of expected result records from a set of known input records. As such, each expected result record, for example, the de-identified electronic record 145, may be associated with a corresponding known input record, for example, the electronic record 135.

During optimization, the processing engine 120 may de-identify a known input record to produce a test result record, for example, the de-identified electronic record 145. The de-identification system 100 may compare the test result record with the corresponding expected result record to determine whether an error occurred during the de-identification process.

If a token appears in the test result record but is obfuscated in the expected result record, the processing engine 120 may be allowing some protected health information tokens to appear in the de-identified electronic record 145. In some example embodiments, this type of error may be referred to as a recall error.

If, on the other hand, if a token is obfuscated in the test result record but is not obfuscated in the expected result record, the processing engine 120 may be obfuscating tokens that are not considered protected health information, and, as such, do not need to be obfuscated. In some example embodiments, this type of error may be referred to as a precision error.

To correct for a recall error and/or precision error, the de-identification system 100 may modify one or more de-identification configurations in the de-identification configuration library 215, one or more filters in the filters library 225, one or more whitelists in the whitelist library 235, and/or one or more blacklists in the blacklist library 245.

In some example embodiments, the de-identification system 100 may correct for a recall error and/or precision error by changing the sequence of operations performed during the de-identification process. Changing the sequence of operations may include, for example, adding a new operation, deleting an operation, performing an operation earlier in the de-identification process, performing an operation later in the de-identification process, and/or the like. For example, the de-identification system 100 may apply the blacklist 240 before or after applying the protected health information filter. The de-identification system 100 may store these changes to the de-identification process in the de-identification configuration 210.

In some example embodiments, the de-identification system 100 may correct for a recall error and/or precision error by modifying the parts-of-speech tags that trigger one or more operations of the de-identification process. For example, the de-identification system 100 may modify the de-identification configuration 210 to indicate the blacklist 240 should be searched for tokens that have been tagged as a first part-of speech (e.g., nouns) instead of a second-part-of-speech (e.g., pronouns) if the triggering the search of the blacklist 240 based on tokens being tagged as the first part-of-speech results in a threshold quantity of recall errors and/or precision errors.

In some example embodiments, the de-identification system 100 may correct for a recall error and/or precision error by modifying the parts of speech tagging algorithm applied to determine the parts of speech of the tokens. Alternatively and/or additionally, the de-identification system 100 may correct for a recall error and/or precision error by changing the parts of speech tagging algorithm that is applied to determine the parts of speech of each token. For example, the de-identification system 100 may analyze the parts of speech using a machine learning model instead of or in addition to the Python Natural Language Toolkit. The de-identification system 100 may store these changes to the parts of speech tagging module in the de-identification configuration 210.

In some example embodiments, to correct for a recall error (e.g. when protected health information incorrectly appears in the test result record), the de-identification system 100 may create an unsafe regular expression and create or modify a filter to include the unsafe regular expression. Alternatively and/or additionally, the de-identification system 100 may remove one or more tokens from a whitelist and/or add the tokens to a blacklist.

In some example embodiments, to compensate for a precision error (e.g. when a safe token is needlessly obfuscated in the test result record), the de-identification system 100 may create a safe regular expression and create or modify a filter to include the safe regular expression. Alternatively and/or additionally, the processing engine 120 may add one or more tokens to a whitelist and/or remove one or more tokens from a blacklist.

In some example embodiments, the de-identification system may create and/or modify a de-identification configuration to include any changes made to the filters, blacklists, and/or whitelists.

Figure 4:
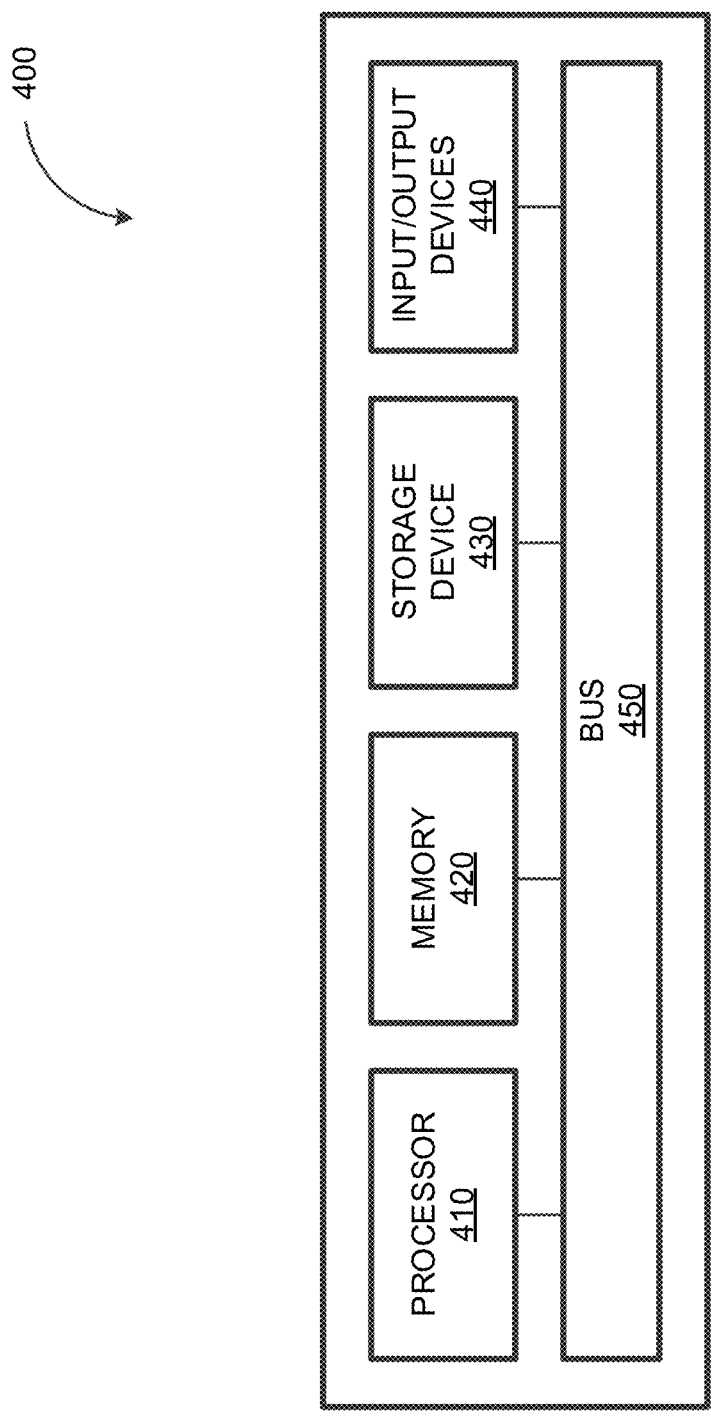
FIG. 4 depicts a block diagram illustrating a computing system, in accordance with some example embodiments.

FIG. 4 depicts a block diagram illustrating a computing system 400, in accordance with some example embodiments. Referring to FIGS. 1-4, the computing system 400 may be used to implement the processing engine 120 and/or any components therein.

As shown in FIG. 4, the computing system 400 can include a processor 410, a memory 420, a storage device 430, and input/output devices 440. The processor 410, the memory 420, the storage device 430, and the input/output devices 440 can be interconnected via a system bus 450. The processor 410 is capable of processing instructions for execution within the computing system 400. Such executed instructions can implement one or more components of, for example, the processing engine 120. In some implementations of the current subject matter, the processor 410 can be a single-threaded processor. Alternately, the processor 410 can be a multi-threaded processor. The processor 410 is capable of processing instructions stored in the memory 420 and/or on the storage device 430 to display graphical information for a user interface provided via the input/output device 440.

The memory 420 is a computer readable medium such as volatile or non-volatile that stores information within the computing system 400. The memory 420 can store data structures representing configuration object databases, for example. The storage device 430 is capable of providing persistent storage for the computing system 400. The storage device 430 can be a floppy disk device, a hard disk device, an optical disk device, or a tape device, or other suitable persistent storage means. The input/output device 440 provides input/output operations for the computing system 400. In some implementations of the current subject matter, the input/output device 440 includes a keyboard and/or pointing device. In various implementations, the input/output device 440 includes a display unit for displaying graphical user interfaces.

According to some implementations of the current subject matter, the input/output device 440 can provide input/output operations for a network device. For example, the input/output device 440 can include Ethernet ports or other networking ports to communicate with one or more wired and/or wireless networks (e.g., a local area network (LAN), a wide area network (WAN), the Internet).

In some implementations of the current subject matter, the computing system 400 can be used to execute various interactive computer software applications that an be used for organization, analysis and/or storage of data in various (e.g., tabular) format. Alternatively, the computing system 400 can be used to execute any type of software applications. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 440. The user interface can be generated and presented to a user by the computing system 400 (e.g., on a computer screen monitor, etc.).

One or more aspects or features of the subject matter described herein can be realized in digital electronic circuitry, integrated circuitry, specially designed application-specific integrated circuit (ASIC), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively and/or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. For example, the logic flows may include different and/or additional operations than shown without departing from the scope of the present disclosure. One or more operations of the logic flows may be repeated and/or omitted without departing from the scope of the present disclosure. Other implementations may be within the scope of the following claims.

What is claimed is:

1. A system, comprising:
at least one data processor; and
at least one memory storing instructions, which when executed by the at least one data processor, result in operations comprising:
tokenizing an electronic record to produce a plurality of tokens including a first token;
determining whether a protected health information is included in the electronic record by at least:
determining whether the first token is part of one of a first plurality of expressions, each of the first plurality of expressions known to include the protected health information, and
in response to determining that the first token is not part of any one of the first plurality of expressions, determining, based on a blacklist of tokens known to comprise the protected health information, whether the first token comprises the protected health information;
in response to determining that the first token comprises the protected health information, generating a de-identified electronic record by at least replacing the first token with a second token obfuscating the protected health information; and
responding to an incorrect identification of the protected health information by at least updating the first plurality of expressions, the first plurality of expressions being updated by at least adding, to the first plurality of expressions, an expression including the first token and a third token adjacent to the first token in the electronic record.

2. The system of claim 1, further comprising:
responding to the incorrect identification of the protected health information by at least updating the blacklist of tokens, the blacklist of tokens being updated by at least adding the first token to the black list of tokens or removing the first token from the blacklist of tokens.

3. The system of claim 1, wherein determining whether the first token comprises the protected health information further comprises assigning a part-of-speech to the first token.

4. The system of claim 3, further comprising:
responding to the incorrect identification of the protected health information by at least modifying the part-of-speech assigned to the first token, the part-of-speech assigned to the first token being modified by at least modifying a first part-of-speech tagging algorithm applied to assign the part-of-speech to the first token and/or changing the first part-of-speech tagging algorithm to a second part-of-speech tagging algorithm.

5. The system of claim 3, further comprising:
in response to the first token being assigned a first part-of-speech, determining, based on the blacklist of tokens known to comprise the protected health information, whether the first token comprises the protected health information.

6. The system of claim 5, further comprising:
responding to the incorrect identification of the protected health information by at least applying the blacklist of tokens in response to the first token being assigned a second part-of-speech instead of the first part-of-speech.

7. The system of claim 1, further comprising:
in response to determining that the first token comprises neither the protected health information nor a non-protected health information, generating the de-identified electronic record by at least replacing the first token with the second token obfuscating the protected health information.

8. The system of claim 1, further comprising:
determining whether the first token comprises a non-protected health information by at least determining whether the first token is part of one of a second plurality of expressions, each of the second plurality of expressions known to exclude the protected health information.

9. The system of claim 1, further comprising:
determining whether the first token comprises the protected health information based at least on a notes map including one or more note-specific unsafe regular expressions, one or more note-specific blacklists, and/or one or more note-specific parts of speech.

10. A computer-implemented method, comprising:
tokenizing an electronic record to produce a plurality of tokens including a first token;
determining whether a protected health information is included in the electronic record by at least
determining whether the first token is part of one of a first plurality of expressions, each of the first plurality of expressions known to include the protected health information, and
in response to determining that the first token is not part of any one of the first plurality of expressions, determining, based on a blacklist of tokens known to comprise the protected health information, whether the first token comprises the protected health information;
in response to determining that the first token comprises the protected health information, generating a de-identified electronic record by at least replacing the first token with a second token obfuscating the protected health information; and
responding to an incorrect identification of the protected health information by at least updating the first plurality of expressions, the first plurality of expressions being updated by at least adding, to the first plurality of expressions, an expression including the first token and a third token adjacent to the first token in the electronic record.

11. The method of claim 10, further comprising:
responding to the incorrect identification of the protected health information by at least updating the blacklist of tokens, the blacklist of tokens being updated by at least adding the first token to the black list of tokens or removing the first token from the blacklist of tokens.

12. The method of claim 10, wherein determining whether the first token comprises the protected health information further comprises assigning a part-of-speech to the first token.

13. The method of claim 12, further comprising:
responding to the incorrect identification of the protected health information by at least modifying the part-of-speech assigned to the first token, the part-of-speech assigned to the first token being modified by at least modifying a first part-of-speech tagging algorithm applied to assign the part-of-speech to the first token and/or changing the first part-of-speech tagging algorithm to a second part-of-speech tagging algorithm.

14. The method of claim 12, further comprising:
in response to the first token being assigned a first part-of-speech, determining, based on the blacklist of tokens known to comprise the protected health information, whether the first token comprises the protected health information.

15. The method of claim 14, further comprising:
responding to the incorrect identification of the protected health information by at least applying the blacklist of tokens in response to the first token being assigned a second part-of-speech instead of the first part-of-speech.

16. The method of claim 10, further comprising:
in response to determining that the first token comprises neither the protected health information nor a non-protected health information, generating the de-identified electronic record by at least replacing the first token with the second token obfuscating the protected health information.

17. The method of claim 10, further comprising:
determining whether the first token comprises a non-protected health information by at least determining whether the first token is part of one of a second plurality of expressions, each of the second plurality of expressions known to exclude the protected health information.

18. The method of claim 10, further comprising determining whether the first token comprises the protected health information based at least on a notes map including one or more note-specific unsafe regular expressions, one or more note-specific blacklists, and/or one or more note-specific parts of speech.

* * * * *